US008119345B2

(12) United States Patent
Weusten et al.

(10) Patent No.: US 8,119,345 B2
(45) Date of Patent: Feb. 21, 2012

(54) METHOD FOR DISCRIMINATING SINGLE NUCLEOTIDE POLYMORPHISMS

(75) Inventors: Jos Weusten, Horst aan de Maas (NL); Maarten J. D. De Kock, Voorhout (NL)

(73) Assignee: Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 12/448,208

(22) PCT Filed: Feb. 5, 2008

(86) PCT No.: PCT/EP2008/000883
§ 371 (c)(1),
(2), (4) Date: Jun. 29, 2009

(87) PCT Pub. No.: WO2008/095680
PCT Pub. Date: Aug. 14, 2008

(65) Prior Publication Data
US 2010/0041038 A1    Feb. 18, 2010

(30) Foreign Application Priority Data
Feb. 6, 2007   (EP) ..................................... 07075101

(51) Int. Cl.
*C12Q 1/68* (2006.01)
(52) U.S. Cl. ....................................................... 435/6.1
(58) Field of Classification Search .................. None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 5,405,950 | A | 4/1995 | Mock et al. |
| 5,633,364 | A | 5/1997 | Mock et al. |

FOREIGN PATENT DOCUMENTS

| EP | 0 569 272 A1 | 11/1993 |
| EP | 0 329 822 B1 | 6/1994 |
| EP | 1 366 179 A2 | 12/2003 |
| FR | 2 607 507 A1 | 6/1988 |
| WO | WO 90/01069 A1 | 2/1990 |
| WO | WO 90/06995 A1 | 6/1990 |
| WO | WO 97/46707 A2 | 12/1997 |
| WO | WO 03/062791 A2 | 7/2003 |
| WO | WO 03062791 A2 * | 7/2003 |

OTHER PUBLICATIONS

Berard Cecile et al. ( "DNAnucleic acid sequence-based amplification-based genotyping for polymorphism analysis" Biotechniques, vol. 37, No. 4, Oct. 2004, pp. 680-684).*

Berard et al. (Biotechniques. Oct. 2004;37(4):680-2, 684, 686).*
Weusten et al.,"Principles of quantitation of viral loads using nucleic acid sequence-based amplification in combination with homogeneous detections using molecular beacons," *Nucleic Acids Research*, 2002, pp. 1-7, vol. 30, No. 6, e26.
Egholm et al., "Peptide Nucleic Acids (PNA). Oligonucleotide Analogues with an Achiral Peptide Backbone," *J. Am. Chem. Soc.*, 1992, pp. 1895-1897, vol. 114.
Piatek et al., "Molecular beacon sequence analysis for detecting drug resistance in *Mycobacterium tuberculosis*," *Nature Biotechnology*, Apr. 1998, pp. 359-363, vol. 16.
Tyagi et al., "Molecular Beacons: Probes that Fluoresce upon Hybridization," *Nature Biotechnology*, Mar. 1996, pp. 303-308, vol. 14.
Berard et al., "DNA nucleic acid sequence-based amplification-based genotyping for polymorphism analysis," *BioTechniques*, Oct. 2004, pp. 680-686, vol. 37, No. 4.
Ayele et al., "Development of a nucleic acid sequence-based amplification assay that uses *gag*-based molecular beacons to distinguish between human immunodeficiency virus type 1 subtype C and C' infections in Ethiopia," *Journal of Clinical Microbiology*, Apr. 2004, pp. 1534-1541, vol. 42, No. 4.
Beuningen et al., "Development of a high throughput detection system for HIV-1 using real-time NASBA based on molecular beacons," *Genomics and Proteomics Technologies: Proceedings of SPIE*, 2001, pp. 66-72, vol. 4264.
Leone et al, "Molecular beacon probes combined with amplification by NASBA enable homogeneous, real-time detection of RNA," *Nucleic Acids Research*, 1998, pp. 2150-2155, vol. 26, No. 9.
Marras et al., "Real-time assays with molecular beacons and other fluorescent nucleic acid hybridization probes," *Clinica Chimica Acta Amsterdam*, Jan. 2006, pp. 48-60, vol. 363, No. 1-2.
Marras et al., "Multiplex detection of single-nucleotide variations using molecular beacons", *Genetic Analysis: Biomolecular Engineering*, 1999, pp. 151 -156, vol. 14.
Russom et al., "Single nucleotide polymorphism analysis by allele-specific primer extension with real-time bioluminescence detection in a microfluidic device," *Journal of Chromatography*, Oct. 2003, pp. 37-45, vol. 1014.

* cited by examiner

*Primary Examiner* — Christopher M. Babic
(74) *Attorney, Agent, or Firm* — Oliff & Berridge, PLC

(57) ABSTRACT

A method for discriminating single nucleotide polymorphisms (SNPs) offers improved sensitivity and specificity. A test kit is also provided. The method may be for genotyping in typing assays applied to a biological sample. The method may include steps of performing a real-time amplification of the target, generating multiple copies of amplicons, in presence of at least two different labeled probes, each probe allowing real-time detection at the SNP position of both the wildtype and at least one possible mutation, assessing the discriminatory variable value(s) based on the signals of each combination of two detection probes, and discriminating between the genotypes. The methods may be for diagnostic, preventive and therapeutic applications.

20 Claims, 1 Drawing Sheet

METHOD FOR DISCRIMINATING SINGLE NUCLEOTIDE POLYMORPHISMS

Figure 1:
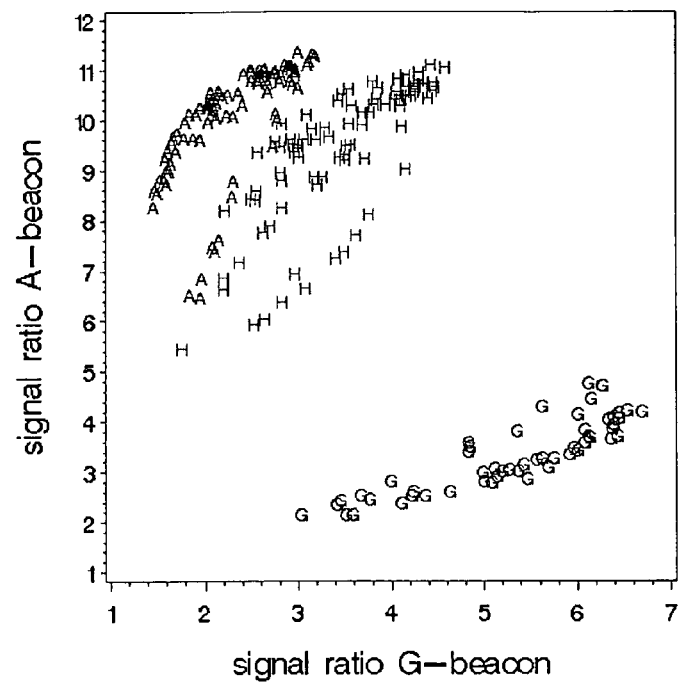

The present invention provides a method for discriminating single nucleotide polymorphisms (SNPs) which offers improved sensitivity and specificity.

A single nucleotide polymorphism (SNP) is a single base change or point mutation but also includes the so-called "indel" mutations (insertions or deletions of a nucleotide), resulting in genetic variation between individuals. SNPs, which make up about 90% of all human genetic variation, occur every 100 to 300 bases along the 3-billion-base human genome. However, SNPs can occur much more frequently in other organisms like viruses. SNPs can occur in coding or non-coding regions of the genome. A SNP in the coding region may or may not change the amino acid sequence of a protein product. A SNP in a non-coding region can alter promoters or processing sites and may affect gene transcription and/or processing. Knowledge of whether an individual has particular SNPs in a genomic region of interest may provide sufficient information to develop diagnostic, preventive and therapeutic applications for a variety of diseases.

There are many methods for genotyping SNPs. A key requirement of a SNP genotyping method is that it distinguishes unequivocally between the allelic variants present. As humans are diploid, there are three possible genotypes for a biallelic SNP: the patient has a homozygous wildtype sequence, a homozygous mutated sequence, or the heterozygous sequence. The majority of these methods can be separated into four groups based on molecular mechanisms: Allele Specific Hybridization, Allele Specific Oligonucleotide Ligation, Primer Extension, Sequencing.

More recently, the advent of real-time PCR allowed the development of homogeneous methods for SNP detection such as melting curve analysis of FRET probes and 5' fluorogenic nuclease assay, also known as the TaqMan® assay. These methods are attractive because signal amplification and allele detection are accomplished in a single, closed tube. They use fluorogenic allele-specific oligonucleotide (ASO) probes and are generally carried out on real-time thermocyclers comprising an integrated fluorimeter. These methods require appropriate probe design as well as buffer composition and adjustment of the PCR cycling conditions. Thus, in these cycling conditions, one of the most important variables to be optimized is the annealing temperature ($T_a$) which is the temperature allowing the binding of the primers to single DNA strands. A low $T_a$ may cause the synthesis of nonspecific PCR products while the use of a high $T_a$ may reduce the yield of a desired PCR product. Consequently, the use of optimal $T_a$ minimizes, but does not avoid, the cross-hybridization of target DNA to a primer even in the presence of a mismatch. The difference in efficiency of PCR amplification between the primers may not be sufficiently large to permit easily discrimination between the normal nucleotide and the mutated nucleotide.

In order to improve SNP detection by PCR real-time, the fluorescence monitoring has been optimized.

Melting-curve analysis of FRET hybridisation probes is a technology patented by University of Utah (WO-A-97/46707). In its simplest configuration, the reaction mixture includes two oligonucleotide probes, that hybridize to adjacent regions of the target sequence. The adjacent 3' and 5' ends of the two probes are labelled with fluorescent dyes. Fluorescent light emitted by the "donor" excites the "acceptor" fluorophore creating a unique fluorogenic complex. The complex is only formed when the probes bind to adjacent sites on amplified DNA. Once PCR amplification is complete, a "melting curve" is generated by slowly heating the amplicon/probe heteroduplex and measuring the changes in fluorescence that result from dissociation of the probe and the amplicon. The principle of melting curve analysis is that each double-stranded DNA has its own specific melting temperature (Tm), which is defined as the temperature at which 50% of the DNA becomes single stranded. Thus, temperature curve differs for the normal and mutant alleles. Single-nucleotide mismatch between the mutated probe and the wildtype allele causes the probe to dissociate or melt at a lower temperature than the complex formed with the mutant allele.

While this technology can be used to identify SNPs in a nucleic acid, it nonetheless suffers from some drawbacks in practical applications. As the differences in sequences between the two types of alleles are very small, it is very well possible that a probe designed to preferentially bind to one type of amplicon also shows binding to the other amplicon's type. For example, in the case of substitution as SNP, the effect on the melting kinetics of PCR products is too small to be detected reliably.

A common alternative to the melting curve approach is to use hydrolysis (TaqMan®) probes. This technique is disclosed in international application WO-A-92/02638. The 5'-exonuclease assay uses FRET quenching to analyse Polymerase Chain Reaction (PCR) amplified target DNA. The probes are oligonucleotides that contain fluorophore and quencher moieties preferably located on 5' and 3' termini. The approach uses two labelled ASO probes complementary to the mutant and normal alleles. The two probes hold different fluorescent reporter dyes, but share a common quencher dye. When intact, the probes do not fluoresce due to proximity of the reporter and quencher dyes. During the annealing phase of PCR, the two probes compete for hybridization to their target sequences, downstream of the primer sites. The hybridised probe is subsequently cleaved by the 5'-nuclease activity of *Thermophilus aquaticus* (Taq) polymerase as the primer is extended. This results in separation of the reporter dyes from the quencher causing significant increases in fluorescence emission. Genotyping is determined by measurement of the fluorescence intensity of the two reporter dyes after PCR amplification. Since TaqMan® probes are digested during real-time PCR amplification, probes are not available for post-amplification melting curve analysis. Exploiting this classic 5'-nuclease assay technology, a temperature-independent fluorescence signal is generated during the PCR process by the exonuclease degradation of a hybridized TaqMan probe.

This method needs a careful design of the probes to permit discrimination of polymorphic targets, as preferentially perfectly matched probes are degraded and generate increases in fluorescence signal. As stated above for melting curve analysis, this technique generates similar problems of risk of artifacts.

Thus, there is still a demand for highly sensitive methods that are useful for determining SNP in nucleic acid sequences.

Real-time amplification has allowed the development of qualitative assays for SNP genotyping as exposed above, but also of quantitative assays for gene expression or viral load measurement. In these fields, the datas obtained during amplification are used to determine the amount of target nucleic acid in the original sample. A lot of studies have been necessary to perform quantitative assays and several methods exist. In case of the NASBA amplification process associated with molecular beacons detection, a method for quantification of viral loads has been described in Nucleic Acids Research, 2002, vol. 30, No 6 e26. This method allows to determine the amount of HIV-1 RNA in an original sample.

The assessment of this amount is based on kinetics of the fluorescence generated by the combination of both the transcription rate of the NASBA and by the association rate of the beacon with its specific amplicon/target. When wildtype RNA (WT) is co-amplified in the presence of a fixed amount of calibrator RNA (Q), a quantitation variable is determined by the quotient of:

$$k_{1,WT} V_{WT}/k_{1,Q} V_Q$$

with $k_{1,RNA}$ (representing $k_{1,WT}$ and $k_{1,Q}$) the reaction rate constant of the molecular beacon binding and $V_{RNA}$ (representing $V_{WT}$ and $V_Q$) the transcription rate. Lots of studies with HIV-1 assays have shown that this quantitation variable is indeed a robust estimator for the concentration of WT RNA at fixed calibrator RNA concentrations.

Contrary to all expectations, the inventors of the present invention have found that the quantitation variable cited above $k_{1,WT} V_{WT}/k_{1,Q} V_Q$, as is used for quantitative NASBA-based assays, can be used as a discriminatory variable for SNP genotyping assays, with much better results than classification based on the fluorescence signals alone.

Thus, the present invention is a method for genotyping in typing assays applied to a biological sample, the sample containing one nucleic acid target of interest, the target nucleic acid being susceptible to contain a single nucleotide polymorphism (SNP), comprising the steps of:
  performing a real-time amplification of the target, generating multiple copies of amplicons, in presence of at least two different labeled probes, each probe allowing real-time detection at the SNP position of both the wild-type and at least one possible mutation,
  assessing the discriminatory variable value(s) based on the signals of each combination of two detection probes, and discriminating between the genotypes.

In case of biallelic assay, the discrimination between genotypes takes place for identifying heterozygous mutant from homozygous wildtype or homozygous mutant.

The discriminatory power of the discriminatory variable value is based on the relative association reaction rate constants ($k_1$) since the transcription rate ratios cancel out, as is explained below.

In typing assays, the theory behind the $k_1$ values is more complex than for quantitative assays with well-designed calibrators due to the cross-reactivity of the probes to different types of amplicons. Thus, for bi-allelic typing assays, four binding reaction rate constants have to be distinguished:
  $k_{WT \to WT}$: reflecting the reaction rate constant of a wildtype probe binding with a wildtype amplicon,
  $k_{WT \to m}$: reflecting the reaction rate constant of a wildtype probe binding with a mutated amplicon,
  $k_{m \to WT}$: reflecting the reaction rate constant of a mutated probe binding with a wildtype amplicon,
  $k_{m \to m}$: reflecting the reaction rate constant of a mutated probe binding with a mutated amplicon.

Due to the specificity of the probes, the value of $k_{m \to WT}$ is considerably smaller than the value of $k_{WT \to WT}$ and similarly this statement applies also to $k_{WT \to m}$ regarding $k_{m \to m}$.

Although typing assays are by definition not quantitative in nature, the quantitation variable that can be derived from the two fluorescence curves can be used as discriminatory variable for classification. To explain this, consider a bi-allelic typing assay. In case of a homozygous sample, there is only one type of amplicon RNA, and both beacons bind to it. Thus, the transcription rate refers only to one type of amplicon (Wild-Type or mutated amplicon).

If we consider the amplification of wildtype homozygous target, the signal generated by wildtype probe is used to assess the value $k_{WT \to WT} V_{WT}$ with $V_{WT}$ the transcription rate of wildtype amplicon. As this amplicon is the only one produced, the signal generated by the mutated probe is used to assess the value of $k_{m \to WT} V_{WT}$. Therefore, the quotient used in quantitative assays $k_{1,WT} V_{WT}/k_{1,Q} V_Q$ reduces to $k_{WT \to WT} V_{WT}/k_{m \to WT} V_{WT}$ that in turn reduces to $k_{WT \to WT}/k_{m \to WT}$ since the transcription rate cancels out. Consequently, according to one embodiment of the method the assessment of the discriminatory variable value for the homozygous wildtype is realized by assessment of the ratio $k_{WT \to WT}/k_{m \to WT}$ or its reciprocal.

Similarly, for the homozygous mutated-genotype the quotient reduces to $k_{WT \to m} V_m/k_{m \to m} V_m$ and subsequently to $k_{WT \to m}/k_{m \to m}$. It will be clear that the first ratio ($k_{WT \to WT}/k_{m \to WT}$) will numerically be considerably larger than the second ($k_{WT \to m}/k_{m \to m}$). Consequently, according to one embodiment of the method the assessment of the discriminatory variable value for the homozygous mutant type is realized by assessment of the ratio $k_{WT \to m}/k_{m \to m}$ or its reciprocal.

In case of the heterozygous genotype, there are two different targets. When the starting materials of amplification is DNA, it will be clear that the concentrations of the amplicons in the sample after amplification are identical since both alleles are present in the same amount. Also, due to the very small difference in the target sequence, the transcription rates of the amplicons will be considered as identical. The quotient now reduces to a combination of $k_{WT \to WT}$ and $k_{wt \to m}$ in the numerator, reflecting binding of the wildtype probe, and a combination of $k_{m \to m}$ and $k_{m \to WT}$ in the denominator, reflecting binding of the mutated probe. Due to the equal concentrations of the two genes this combination is an addition and the quotient is therefore $(k_{WT \to WT} + k_{WT \to m})/(k_{m \to m} + k_{m \to WT})$. Consequently, according to one embodiment of the method the assessment of the discriminatory variable value for the heterozygous type is realized by assessment of the ratio $(k_{WT \to WT} + k_{WT \to m})/(k_{m \to m} + k_{m \to WT})$ or its reciprocal.

A skilled worker appreciates that it is possible starting from the teaching of the present invention, to use ratios for assessing presence of SNP, which can deviate slightly from the ratio according to the invention above mentioned but which function nevertheless. For instance instead of an addition, a subtraction, multiplication or divisional operation are also conceivable. Any other solutions making use of these ratios will fall under the scope of protection of said invention.

Since the transcription rate ratios cancel out and only probe binding rates remain, the observed discriminating variable value is independent of the exact amount of target, primers and enzymes, and independent of the activity of enzymes. Thus, the discriminatory variable value can be useful in genotyping assays involving other amplification methods than NASBA, like for example PCR.

According to one embodiment of the method the assessment of the discriminatory variable value for each combination of two detection probes is realized by assessment of the relative association reaction rate constants ($k_1$) of the reactions in which the two detection probes bind to the amplicons.

According to another embodiment of the method, the assessment of the discriminatory variable value for each combination of two detection probes is realized by assessment of the relative dissociation reaction rate constants ($k_2$) of the reactions in which the two detection probes dissociate from the amplicons.

Thus, the assessment of the discriminatory variable value for each detection probe allows to determine the genotype. The scale in which the discriminatory variable is expressed can be divided into ranges using thresholds, the values of which depend on probe properties.

Consequently, according to one embodiment of the method, the ranges of values the discriminatory variables as derived from a combination of two probe signals can attain can be divided in ranges using thresholds, such that the values the discriminatory variables can attain for each genotype cluster in one of these ranges.

In case of a biallelic SNP, the values the discriminatory variable can attain are divided in three ranges using thresholds:

a lower range will contain
- the cluster of homozygous wildtype if the first probe permits detection of the mutant type whereas the second probe permits detection of the wild type. The first and second probes make reference to reaction rate position in the ratio of discriminatory variable. The reaction rate of the first probe is at the numerator and the reaction rate of second probe is at the denominator.
- the cluster of homozygous mutant type if the first probe permits detection of the wildtype whereas the second probe permits detection of the mutant type.

an upper range will contain
- the cluster of homozygous wildtype if the first probe permits detection of the wildtype whereas the second probe permits detection of the mutant type.
- the cluster of homozygous mutant type if the second probe permits detection of the wildtype whereas the first probe permits detection of the mutant type.

a middle range (between the lower and upper range, and not overlapping) will contain the cluster of the heterozygous type.

According to another embodiment, the present invention is a method for genotyping in multi-allelic typing assays where more than two genetic categories have to be detected.

In case two probes have to be used, the same principles as exposed above are applied, but the range of values the discriminatory value can attain is to be divided in more than three ranges. For example, for tri-allelic typing assays, one range will contain the cluster of results for three WT alleles, one range the results for two wildtype and one mutant allele, one range for one wildtype and two mutant alleles, and the fourth the results of three mutant alleles.

For tri-allelic typing assays the genotypes can be, for example, AAA, AAG, AGG and GGG. Similarly as for the bi-allelic typing assays, the discriminatory variable assesses $k_{1,A\_A}/k_{1,G\_A}$, $(2k_{1,A\_A}+k_{1,A\_G})/(2k_{1,G\_A}+k_{1,G\_G})$, $(k_{1,A\_A}+2k_{1,A\_G})/(k_{1,G\_A}+2k_{1,G\_G})$ and $k_{1,A\_G}/k_{1,G\_G}$, respectively. This leads then to four different ranges, the two middle groups being closest to each other.

In case three or more probes have to be used, discriminatory variable values can be derived for each combination of two fluorescence curves. Multidimensional classification strategies, using the same principles, are to be used.

Preferably, the probe contains one or more nucleotides and/or nucleotide analogues that have an affinity increasing modification. The sensitivity to polymorphisms is lowered because the affinity of the probe to the polymorphic site is increased. Thus, the probe can recognize several amplicons, each amplicon containing a different SNP known or unknown. Likewise, it is conceivable that individual or some nucleotides of a primer are replaced with other nucleotides, as long as the specificity of said primers and the melting temperature of said primers are not altered too much. It is evident to the skilled worker that, apart from the usual nucleotides A, G, C and T, modified nucleotides such as inosin, 2'-O-methyl, etc. may also be applied in primers and probes. Other examples are at least one nucleotide containing a modified base such as 5-methyldeoxycytidine, 5-dimethylaminodeoxyuridine, deoxyuridine, 2,6-diaminopurine, 5-bromodeoxyuridine or any other modified base allowing hybridization. Additional modified nucleotides are found in U.S. Pat. Nos. 5,405,950 and 5,633,364 (both, Mock and Lovern). The teaching of the present invention makes such modifications possible, starting from the subject matter of the claims.

According to one embodiment of the method, the amplification is performed by contacting the sample with a pair of primers, the forward and reverse primers being on both sides of the SNP position. When NASBA process is performed, the forward primer being downstream and the reverse primer being upstream of the SNP position. In case of PCR amplification is performed, the forward primer being upstream and the reverse primer being downstream of the SNP position.

According to another embodiment of the method, the real-time amplification is performed by contacting the sample at the same time with a pair of primers and with at least the two labeled probes.

According to any of the embodiments of the method, each probe allows real-time detection by hybridization onto the amplicon, the probe-amplicon hybrid including said SNP position.

Again according to another embodiment of the method, each probe differs from the other(s) by its label that provides distinguishable signal, and by its sequence differing by at least one nucleotide.

The probe sequence corresponds to the wildtype target or to one possible mutation.

In a particular embodiment of the method, the probes are constituted by molecular beacons.

In another particular embodiment of the method, the target nucleic acid sequence is DNA.

Again in another particular embodiment of the method, the amplification reaction is a transcription based amplification method, preferably the NASBA method.

NASBA process is described in European patent no. EP-B-0.329.822. Although this process allows amplification of RNA it can be used to amplificate double stranded nucleic acid as described in the European patent application EP-A-1.366.179. A major advantage of these methods over PCR is that it is performed isothermally.

Another object of the present invention is a test kit for the detection of the genotype in SNP typing assays applied to a biological sample comprising:
- a set of oligonucleotide primers,
- at least two oligonucleotide probes comprising a nucleic acid sequence substantially complementary to at least part of the amplified nucleic acid sequence, one probe dedicated to wild type identification and the other probe dedicated to mutant type identification, each probe being provided with a detectable label, different one another, and
- suitable amplification reagents.

In a particular embodiment of the kit, at least one of the oligonucleotide primer, called forward primer, is associated with an RNA polymerase promoter, preferably a T7 RNA polymerase.

In a particular embodiment of the kit, it further comprises an oligonucleotide probe containing a nucleic acid sequence capable of hybridizing to the region of the nucleic acid amplified using the forward primer and the reverse primer.

Finally the invention concerns a test kit, wherein suitable amplification reagents enable a transcription based amplification method, preferably the NASBA method.

DEFINITIONS

According to the present invention, the term "allele" refers to any of one or more alternative forms of a given gene or DNA segment; both or all alleles of a given gene or DNA segment are concerned with the same trait or characteristic, but the product or function coded by a particular allele differs, qualitatively and/or quantitatively, from that coded by other alleles of that gene or DNA segment.

Thus, the term "multi-allelic" refers to a polymorphic locus characterized by the presence of more than one allele. The term "bi-allelic" refers to a polymorphic locus characterized by two different alleles. Thus, a bi-allelic SNP is a multi-allelic SNP.

The term "genotype" as used herein refers to the identity of the alleles present in an individual or a sample. Typically, one refers to an individual's genotype with regard to a particular gene of interest and, in polyploid individuals, it refers to what combination of alleles the individual carries.

The term "genotyping" consists of determining the specific allele or the specific nucleotide at a polymorphic locus.

By "nucleic acid" (NA) is meant both DNA and RNA, both in any possible configuration, i.e. in the form of double-stranded (ds) nucleic acid, or in the form of single-stranded (ss) nucleic acid, or as a combination thereof (in part ds or ss). Such nucleic acid corresponds to a succession of at least two deoxyribonucleotides or ribonucleotides optionally comprising at least one modified nucleotide.

This polynucleotide may also be modified at the level of the internucleotide bond, such as, for example, phosphorothioates, H-phosphonates, alkyl phosphonates, at the level of the backbone such as, for example, alpha-oligonucleotides (FR-A-2 607 507) or PNAs (M. Egholm et al., J. Am. Chem. Soc., 114, 1895-1897, 1992) or 2'-O-alkylriboses. Each of these modifications may be taken in combination as long as at least one phosphate is present in the nucleic acid. The nucleic acid may be natural or synthetic, an oligonucleotide, a polynucleotide, a nucleic acid fragment, a ribosomal RNA, a messenger RNA, a transfer RNA, a nucleic acid obtained by an enzymatic amplification technique such as:

PCR (Polymerase Chain Reaction), described in U.S. Pat. No. 4,683,195, U.S. Pat. No. 4,683,202 and U.S. Pat. No. 4,800,159, and its RT-PCR (Reverse Transcription PCR) derivative, in particular in a one-step format as described in patent EP-B-0,569,272, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, and TMA (Transcription Mediated Amplification) with U.S.

Such "nucleic acid" may be used as primers and probes. The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. Normally a set of primers will consist of at least two primers, one "upstream" primer and one "downstream" primer, which together define the amplicon (the sequence that will be amplified using said primers).

The "target sequence" is defined as the part of the nucleic acid molecule to be detected. It is amplified by means of the primers and the amplification related enzymes. The amplification leads to formation of "amplicons", which are the nucleic acid molecules that are physically detected by hybridisation to the probe.

As used herein the term "probe" is intended to comprise a stretch of nucleotides hybridising to the amplicon. Preferably the hybridising part is a stretch of 10-50, more preferably 15-35, most preferably 15-30 nucleotides. The probe according to the invention is preferably a so-called molecular beacon (MB). A class of oligonucleotide probes, referred to as molecular beacons, that facilitate homogeneous detection of specific nucleic acid target sequences has been described (Piatek et al. (1998) Nature Biotechnology 16:359-363; Tyagi and Kramer (1996) Nature Biotechnology 14:303-308). Molecular beacons are single-stranded oligonucleotides having a stem-loop structure. The loop portion contains the sequence complementary to the amplicon (either DNA or RNA). The stem is formed due to hydridisation of the complementary sequence of the 3' end with the 5' end. The stem can be unrelated to the amplicon and is double-stranded. One arm of the stem is labelled with a fluorescent dye (fluorophore), whereas the other one is coupled to a quenching moiety. In the stem-loop state the probe does not produce fluorescence because the energy of the fluorophore is transferred to the quenching molecule. When the molecular beacon hybridizes to the amplicon the stem-loop structure is lost and the quencher and fluorophore become separated. At that stage the fluorescence emitted by the fluorophore can be detected and quantified.

The term "discriminatory variable" means a response variable that can be derived from the observed responses of two probes, and that can be used for the final classification. The "discriminatory variable" can be also called the "quantitation variable" that can be derived from the fluorescence curves.

The invention will now be described further, by way of examples, with reference to the accompanying drawings, in which:

FIG. 1 represents the results obtained with a technic according to the state of the art.

The observed fluorescence signal increases for the two molecular beacons signals do not lead to sufficient discrimination.

Legend: A, AA-genotype; G, GG-genotype; H, heterozygous genotype GA.

Figure 2:
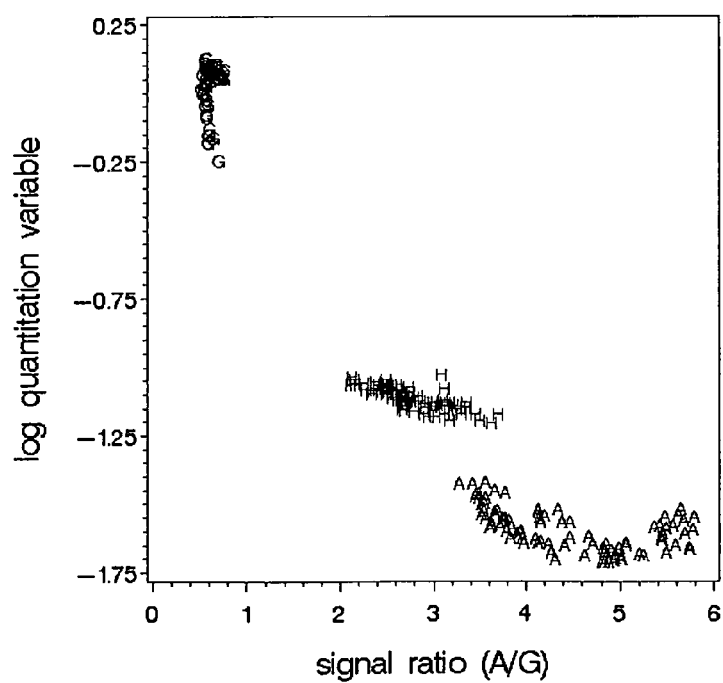

FIG. 2 represents the results obtained with the technic according to the present invention.

The quantitation variable values are plotted on the vertical axis on a log-scale against the ratio of the fluorescence ratios from FIG. 1. The only way the required discrimination between the groups is achieved is based on the quantitation variable value plotted on the vertical axis.

Legend: A, AA-genotype; G, GG-genotype; H, heterozygous genotype GA

EXAMPLE

Thrombosis is a principal human affliction, killing hundreds of thousands and debilitating millions each year by myocardial infarction, pulmonary embolism, or stroke. Risk factors include both hereditary and acquired conditions. Generally, a tendency towards thrombosis could arise from hyperactive coagulation pathways, hypoactive anticoagulant mechanisms, or hypoactive fibrinolysis. Mutations in genes that encode proteins in these pathways play an important role in the predisposition to thrombosis.

One of the possible SNPs concerns the gene coding for one of the clotting factors, that is Factor II. At a specific location, a G (wildtype) or an A (mutant) nucleotide can be present.

Clinical samples from three groups of patients (homozygous wildtype, homozygous mutant and heterozygous) were subjected to the NucliSens EasyQ Factor II assay. In this assay, the genomic DNA is amplified in the presence of both molecular beacons. Due to the accumulation of amplification product, fluorescence signals are generated. A simple measure for the amount of signal is found in the ratio of the maximal observed fluorescence signal in time over the initial background level.

The obvious classification is based on this extent of fluorescence increase:
in case of a homozygous genotype one signal type is expected to dominate (either A or G),
whereas in the heterozygous genotype both signals will make their appearance.

Due to the large homology between the genotypes, however, completely specific beacons can not be developed and as a result, as can be seen from FIG. 1, both signals make their appearance in all three groups. Clearly, the genotype GG group is separated from the other two (GA and AA), but these two show considerable overlap.

As alternative the quantitation variable was used. The results are presented in FIG. 2. On the horizontal axis the ratio of the fluorescence signal increases is presented. Clearly the separation of the quantitation variable values is complete.

Some summary statistics of the quantitation variable values are presented in Table 1 below:

TABLE 1

| Genotype | n | min | max | mean | SD |
|---|---|---|---|---|---|
| AA | 90 | −1.71 | −1.42 | −1.58 | 0.075 |
| GA | 90 | −1.20 | −1.03 | −1.11 | 0.042 |
| GG | 54 | −0.25 | +0.13 | +0.03 | 0.087 |

The invention claimed is:

1. A method for genotyping in typing assays applied to a biological sample, the sample containing a nucleic acid target of interest, the target nucleic acid being susceptible to having a single nucleotide polymorphism (SNP), comprising the steps of:
performing a real-time amplification of the target, generating multiple copies of amplicons, in the presence of at least two different labeled probes, each probe allowing real-time detection at an SNP position of both a wildtype and at least one possible mutation,
actively calculating a discriminatory variable value based on signals of each combination of the at least two different labeled probes, and
discriminating between the genotypes based on the discriminatory variable value,
wherein:
when the SNP is a bi-allelic SNP, the discriminatory variable value for a heterozygous genotype is a ratio selected from the group consisting of $(k_{WT \to WT}+k_{WT \to m})/(k_{m \to m}+k_{m \to WT})$, $(k_{WT \to WT}-k_{WT \to m})/(k_{m \to m}-k_{m \to WT})$, $(k_{WT \to WT} \times k_{WT \to m})/(k_{m \to m} \times k_{m \to WT})$, $(k_{WT \to WT}/k_{WT \to m})/(k_{m \to m}/k_{m \to WT})$, and their reciprocals;
the discriminatory variable value for a homozygous mutant genotype is a ratio of $k_{WT \to m}/k_{m \to m}$ or its reciprocal;
the discriminatory variable value for a homozygous wildtype is a ratio of $k_{WT \to WT}/k_{m \to WT}$ or its reciprocal;
when the SNP is a tri-allelic SNP, the discriminatory variable value for an AAA genotype is a ratio of $k_{A\_A}/k_{G\_A}$ or its reciprocal;
the discriminatory variable value for an AAG genotype is a ratio selected from the group consisting of $(2k_{A\_A}+k_{A\_G})/(2k_{G\_A}+k_{G\_G})$, $(2k_{A\_A}-k_{A\_G})/(2k_{G\_A}-k_{G\_G})$, $(2k_{A\_A} \times k_{A\_G})/(2k_{G\_A} \times k_{G\_G})$, $(2k_{A\_A}/k_{A\_G})/(2k_{G\_A}/k_{G\_G})$, and their reciprocals;
the discriminatory variable value for an AGG genotype is a ratio selected from the group consisting of $(k_{A\_A}+2k_{A\_G})/(k_{G\_A}+2k_{G\_G})$, $(k_{A\_A}-2k_{A\_G})/(k_{G\_A}-2k_{G\_G})$, $(k_{A\_A} \times 2k_{A\_G})/(k_{G\_A} \times 2k_{G\_G})$, $(k_{A\_A}/2k_{A\_G})/(k_{G\_A}/2k_{G\_G})$, and their reciprocals; and
the discriminatory variable value for a GGG genotype is a ratio of $k_{A\_G}/k_{G\_G}$ or its reciprocal.

2. The method according to claim 1, wherein the amplification is performed by contacting the sample with a pair of primers comprising forward and reverse primers being on both sides of the SNP position.

3. The method according to claim 1, wherein the real-time amplification is performed by contacting the sample at the same time with a pair of primers and with the at least two different labeled probes.

4. The method according to claim 1, wherein each probe allows real-time detection by hybridization onto the amplicon, the probe-amplicon hybrid including said SNP position.

5. The method according to claim 1, wherein the at least two different labeled probes differ from one another by its label that provides a distinguishable signal, and by its sequence differing by at least one nucleotide.

6. The method according to claim 5, wherein sequences of the at least two different labeled probes correspond to the wildtype target or to the at least one possible mutation.

7. The method according to claim 1, wherein the discriminatory variable value for each combination of the at least two different labeled probes is a ratio of a relative association reaction rate constant ($k_1$) of reactions in which the at least two different labeled probes bind to the amplicons.

8. The method according to claim 1, wherein the discriminatory variable value for each combination of the at least two different labeled probes is a ratio of a relative dissociation reaction rate constant ($k_2$) of reactions in which the at least two different labeled probes dissociate from the amplicons.

9. The method according to claim 7, wherein ranges of values the discriminatory variables as derived from a combination of signals from the at least two different labeled probes can attain can be divided in ranges using thresholds, such that the values the discriminatory variables can attain for each genotype cluster in one of these ranges.

10. The method according to claim 1, wherein the SNP is a bi-allelic SNP.

11. The method according to claim 10, wherein the values the discriminatory variable can attain are divided into three ranges using thresholds, the three ranges being a lower range, a middle range, and an upper range.

12. The method according to claim 11, wherein the values the discriminatory variable can attain for a heterozygous target are clustered in the middle range.

13. The method according to claim 11, wherein when the values the discriminatory variable can attain are clustered in the lower range, the target sequence is:
homozygous wildtype if a first probe permits detection of the mutant genotype whereas a second probe permits detection of the wildtype, and
homozygous mutant genotype if the first probe permits detection of the wildtype whereas the second probe permits detection of the mutant genotype.

14. The method according to claim 11, wherein when the values the discriminatory variable can attain are clustered in the upper range, the target sequence is:

homozygous wildtype if a first probe permits detection of the wildtype whereas a second probe permits detection of the mutant genotype, and homozygous mutant type if the second probe permits detection of the wildtype whereas the first probe permits detection of the mutant genotype.

15. The method according to claim 1, wherein the probes comprise molecular beacons.

16. The method according to claim 1, wherein the target nucleic acid sequence is DNA.

17. The method according to claim 1, wherein the amplification reaction is a Nucleic Acid Sequence-Based Amplification (NASBA).

18. The method according to claim 1, wherein the SNP is a tri-allelic SNP.

19. A method for genotyping in typing assays applied to a biological sample, the sample containing a nucleic acid target of interest, the target nucleic acid being susceptible to having a single nucleotide polymorphism (SNP), comprising the steps of:

performing a real-time amplification of the target, generating multiple copies of amplicons, in the presence of at least two different labeled probes, each probe allowing real-time detection at an SNP position of both a wildtype and at least one possible mutation, actively calculating a discriminatory variable value based on signals of each combination of the at least two different labeled probes, and discriminating between the genotypes based on the discriminatory variable value; wherein:

the SNP is a bi-allelic SNP;

the discriminatory variable value for a heterozygous genotype is a ratio selected from the group consisting of $(k_{WT \to WT} + k_{WT \to m})/(k_{m \to m} + k_{m \to WT})$, $(k_{WT \to WT} - k_{WT \to m})/(k_{m \to m} - k_{m \to WT})$, $(k_{WT \to WT} \times k_{WT \to m})/(k_{m \to m} \times k_{m \to WT})$, $(k_{WT \to WT}/k_{WT \to m})/(k_{m \to m}/k_{m \to WT})$, and their reciprocals;

the discriminatory variable value for a homozygous mutant genotype is a ratio $k_{WT \to m}/k_{m \to m}$ or its reciprocal;

the discriminatory variable value for a homozygous wildtype is a ratio $k_{WT \to WT}/k_{m \to WT}$ or its reciprocal.

20. A method for genotyping in typing assays applied to a biological sample, the sample containing a nucleic acid target of interest, the target nucleic acid being susceptible to having a single nucleotide polymorphism (SNP), comprising the steps of:

performing a real-time amplification of the target, generating multiple copies of amplicons, in the presence of at least two different labeled probes, each probe allowing real-time detection at an SNP position of both a wildtype and at least one possible mutation, actively calculating a discriminatory variable value based on signals of each combination of the at least two different labeled probes, and discriminating between the genotypes based on the discriminatory variable value; wherein:

the SNP is a tri-allelic SNP;

the discriminatory variable value for an AAA genotype is a ratio of $k_{A \to A}/k_{G \to A}$ or its reciprocal;

the discriminatory variable value for an AAG genotype is a ratio selected from the group consisting of $(2k_{A \to A} + k_{A \to G})/(2k_{G \to A} + k_{G \to G})$, $(2k_{A \to A} - k_{A \to G})/(2k_{G \to A} - k_{G \to G})$, $(2k_{A \to A} \times k_{A \to G})/(2k_{G \to A} \times k_{G \to G})$, $(2k_{A \to A}/k_{A \to G})/(2k_{G \to A}/k_{G \to G})$, and their reciprocals;

the discriminatory variable value for an AGG genotype is a ratio selected from the group consisting of $(k_{A \to A} + 2k_{A \to G})/(k_{G \to A} + 2k_{G \to G})$, $(k_{A \to A} - 2k_{A \to G})/(k_{G \to A} - 2k_{G \to G})$, $(k_{A \to A} \times 2k_{A \to G})/(k_{G \to A} \times 2k_{G \to G})$, $(k_{A \to A}/2k_{A \to G})/(k_{G \to A}/2k_{G \to G})$, and their reciprocals; and the discriminatory variable value for a GGG genotype is a ratio of $k_{A \to G}/k_{G \to G}$ or its reciprocal.

* * * * *